United States Patent [19]

Dininno et al.

[11] Patent Number: 5,247,074

[45] Date of Patent: Sep. 21, 1993

[54] (2-SUBSTITUTED PHENYL) CARBAPENEMS

[75] Inventors: Frank P. Dininno, Old Bridge; Thomas N. Salzmann, North Plainfield, both of N.J.; Eugene D. Thorsett, Moss Beach, Calif.

[73] Assignee: Merck & Co., Inc., Rahway, N.J.

[21] Appl. No.: 888,461

[22] Filed: May 20, 1992

Related U.S. Application Data

[63] Continuation of Ser. No. 594,888, Oct. 9, 1990, abandoned.

[51] Int. Cl.⁵ .................. C07D 487/04; C07F 7/10
[52] U.S. Cl. .................. 540/302; 424/452; 424/489
[58] Field of Search .................. 540/302

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/210 |
| 4,962,101 | 10/1990 | DiNinno et al. | |

FOREIGN PATENT DOCUMENTS 0277743 8/1988 European Pat. Off. .

OTHER PUBLICATIONS

L. D. Cama et al., Total Synthesis or Thienamycin Analogs-III, Tetrahedron 39, 2531 (1983).
R. N. Guthikonda, et al., Structure Activity Relationships in the 2-Arylcarbapenem Series, *J. Med. Chem.*, 30, 871 (1987).

Primary Examiner—Thurman K. Page
Assistant Examiner—Jyothsna Venkat
Attorney, Agent, or Firm—Richard C. Billups; Raymond M. Speer

[57] ABSTRACT

Carbapenems of the formula:

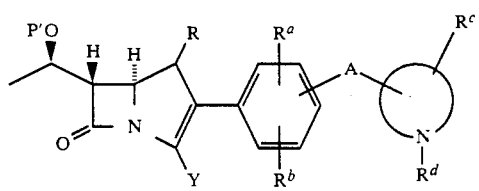

are useful intermediates to antibacterial agents.

3 Claims, No Drawings

(2-SUBSTITUTED PHENYL) CARBAPENEMS

This application is a continuation of Ser. No. 07/594,888, filed Oct. 9, 1990, now abandoned.

BACKGROUND OF THE INVENTION

The present invention relates to antibacterial agents of the carbapenem class, in which the 2-position sidechain is characterized by a phenyl moiety, optionally substituted, to which is attached through an carbonyloxyalkyl or an aminoalkyl bridge, a nitrogen-containing heterocyclic group, with attachment being through a ring carbon atom, to which is attached, in turn, a heterocyclic group, as described in more detail further below.

Thienamycin was an early carbapenem antibacterial agent having a broad spectrum; it has the following formula:

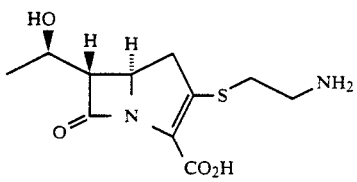

Later, N-formimidoyl thienamycin was discovered; it has the formula:

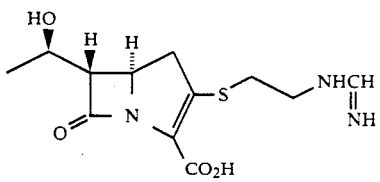

The 2-(heterocyclylalkyl)phenyl carbapenems of the present invention have an antibacterial potency equal to or greater than, in most cases, that of either thienamycin or N-formimidoyl thienamycin. The compounds of the present invention are also more resistant then thienamycin or N-formimidoyl thienamycin to degradation by the dehydropeptidase enzyme DHP-I, thus permitting greater therapeutic application of the compounds.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627, all assigned to Merck & Co., Inc. and incorporated herein by reference, and have the formula:

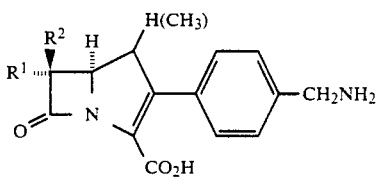

However, these compounds belong to a different class from those of the present invention and are distinguished by different physiological properties.

SUMMARY OF THE INVENTION

The present invention provides novel carbapenem compounds of the formula:

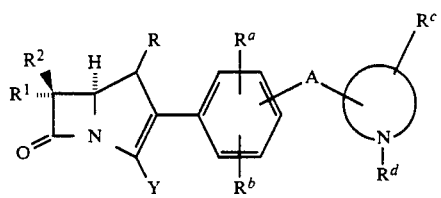

wherein:

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$ and $R^b$, are independently selected from the group consisting of hydrogen and the radicals set out below:

a) a trifluoromethyl group: —$CF_3$;

b) a halogen atom: —Br, —Cl, —F, or —I;

c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —$O(C=O)R^s$, where $R^s$ is $C_{1-4}$ alkyl or phenyl, each of which is optionally mono-substituted by $R^q$ as defined above;

f) a carbamoyloxy radical: —$O(C=O)N(R^y)R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)—, —$S(O)_2$— or —$NR^e$—, to form a ring (where $R^e$ is hydrogen, $C_1$-$C_4$alkyl, and $C_1$-$C_4$alkyl mono-substituted with $R^q$ and the ring is optionally mono-substituted with Rq as defined above);

g) a sulfur radical: —$S(O)_n$—$R^s$ where n=0-2, and $R^s$ is defined above;

h) a sulfamoyl group: —$SO_2N(R^y)R^z$ where $R^y$ and $R^z$ are as defined above;

i) azido: $N_3$ j) a formamido group: —$N(R^f)(C=O)H$, where $R^f$ is H or $C_{1-4}$ alkyl, and the alkyl thereof is optionally mono-substituted by $R^q$ as defined above;

k) a ($C_1$-$C_4$ alkyl)carbonylamino radical: —$N(R^f)(C=O)C_{1-4}$ alkyl, where $R^f$ is as defined above, and the alkyl group is also optionally mono-substituted by $R^q$ as defined above;

l) a ($C_1$-$C_4$ alkoxy) carbonylamino radical: —$N(R^f)(C=O)OC_{1-4}$ alkyl, where $R^f$ is as defined above, and the alkyl group is also optionally mono-substituted by $R^q$ as defined above;

m) a ureido group: —N(R$^t$)(C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as define above;

r) carbonyl radical: —(C=O)R$^s$, where R$^s$ is as defined above;

s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;

t) a (C$_1$-C$_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$-C$_4$ alkoxy)carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono [P=O(OM$^b$)$_2$]; alkylphosphono {P=O(OM$^b$-[O(C$_1$-C$_4$ alkyl)]}; alkylphosphinyl [P=O(OM$^b$)—(C$_1$-C$_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_2$-C$_4$ alkenyl radical, optionally mono-substituted by one of the substituents a) to ab) above and phenyl which is optionally substituted by R$^q$ as defined above;

ad) C$_2$-C$_4$ alkynyl radical, optionally mono-substituted by one of the substituents a) to ab) above;

ae) C$_1$-C$_4$ alkyl radical;

af) C$_1$-C$_4$ alkyl mono-substituted by one of the substituents a)-ab) above;

ag) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to af) above;

R$^x$ is phenyl or heteroaryl, where heteroaryl is as defined below except that there is no quaternary nitrogen and attachment through nitrogen is optional, and the phenyl and heteroaryl are optionally mono-substituted by R$^q$; M$^c$ is hydrogen or an alkali metal; R$^y$ and R$^z$ are as defined above;

R$^c$ is C$_1$-C$_6$ alkyl or R$^q$ defined hereinabove;

R$^d$ is hydrogen, NH$_2$, O or C$_1$-C$_4$alkyl (where the alkyl group is optionally mono-substituted with R$^q$ as defined above);

A is para (p) or meta (m) with respect to the point of attachment of the phenyl ring to the carbapenem nucleus, and is (CH$_2$)$_m$—Q—(CH$_2$)$_n$, where m is 1 to 2 and n is 0 to 2; and Q is O(C=O) or NR$^g$; where R$^g$ is hydrogen or C$_1$-C$_6$ alkyl;

is a aliphatic cyclic hydrocarbon group having 4 or 7 ring atoms in which one of the carbon atoms has been replaced by a nitrogen atom and attachment of said group is by way of a carbon atom in the ring, and in which one carbon atom may be optionally replaced by a heteroatom selected from O and S, and from 1 to 2 additional carbon atoms are optionally replaced by a nitrogen atom, and in which both hydrogens on one or two carbon ring atoms may be replaced by an oxygen atom so as to form a carbonyl moiety; and in which both hydrogen atoms on two adjacent carbons are replaced by an unsaturated hydrocarbon radical so that a fused phenyl ring is formed;

Y is selected from:
i) COOH or a pharmaceutically acceptable ester thereof;
ii) COOM wherein M is an alkali metal or other pharmaceutically acceptable salt;
iii) COOY$^1$ wherein Y$^1$ is a readily removable carboxy covering group and COOY$^1$ is not a pharmaceutically acceptable ester.

Also provided by the present invention are intermediates of the formula:

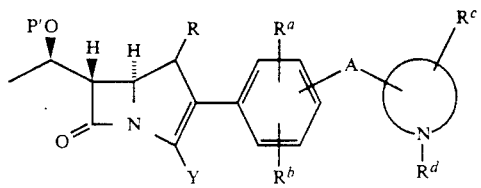

where
R is: H or CH$_3$:

P' is: a readily removable protecting group for hydroxy;

Y is: —COOY' where Y' is a readily removable protecting group for carboxy and —COOY' is not a pharmaceutically acceptable ester; and A, $R^a$, $R^b$, $R^c$ and $R^d$ are defined above, with the proviso that $R^q$ additionally includes OP' where P' is defined above, that $M^a$ and $M^b$ of $R^q$ both include M and that $R^a$ and $R^b$ additionally may be protected hydroxy, OP'.

Utilized in this invention are intermediates of the formula:

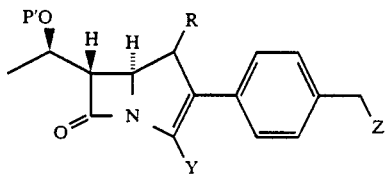

where

R is: H or $CH_3$:

P' is: a readily removable protecting group for hydroxy;

Y is: —COOY' where Y' is a readily removable protecting group for carboxy and —COOY' is not a pharmaceutically acceptable ester; and Z is: selected from the group consisting of alkyl and substituted alkylsulfonates, aryl and substituted arylsulfonates, and halides.

The $R^c$ substituent represents from 1 to 3 substituents which may be the same or different and are selected on an independent basis. A single such substituent is preferred.

It is implied that when the aliphatic cyclic hydrocarbon group has two of the carbon ring atoms replaced by nitrogen atoms each nitrogen atom is substituted by a $R^d$ group.

With reference to the above definitions, "alkyl" means a straight or branched chain aliphatic hydrocarbon radical.

The term "heteroatom" means N, S, or O, selected on an independent basis.

Under the definition of "Y", the term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined. It will also be noted that the compounds of the present invention are potentially internal salts or zwitterions, since under physiological conditions the carboxyl group may be anionic, and this electronic charge will be balanced off internally against the cationic charge of the heteroarylium group. Where this is not the case, it is recognized that a counterion must be present. This counterion is selected from the group of suitable pharmaceutical anions, e.g., chloride, phosphate and tartrate.

As used herein, the term "a readily removable carboxyl covering group which is not a pharmaceutically acceptable ester" means allyl, substituted allyl, benzyl, substituted benzyl, alkyl, substituted alkyl or triorganosilyl. The substituted groups have substituents familiar to those in the art. The term "triorganosilyl" means those silyl groups trisubstituted by lower alkyl groups or aryl groups or combinations thereof and wherein one substituent may be a lower alkoxy. Suitable hydroxyl protecting groups, P', are triorganosilyl groups such as trialkylsilyl, aryl(alkyl)silyl, and diarylalkylsilyl and carbonate groups such as alkyloxycarbonyl and substituted alkyloxycarbonyl, benzyloxycarbonyl and substituted benzyloxycarbonyl and allyloxycarbonyl and substituted allyloxycarbonyl. The preferred protecting groups are methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

It is preferred that $R^1$ is (R)—$CH_3CH(OH)$— or (R)—$CH_3CH(F)$—, and (R)—$CH_3CH(OH)$— is most preferred. It is preferred that $R^2$ is hydrogen. Further, it is preferred that the configuration at C-6 is (S), and that at C-5 is (R).

Representative A groups are —$CH_2NH$—, —$CH_2NHCH_2$—, —$CH_2CH_2OC(O)$—, —$CH_2OC(O)$—, and —$CH_2OC(O)CH_2$—. Preferred is —$CH_2OC(O)$— or —$CH_2NH$—.

It is understood that the chemical formula defining the A spacer is to be read in a normal left to right manner and is not to be read in any other direction. Thus $(CH_2)_m$—Q—$(CH_2)_n$ is not equivalent to, and should not be read as, $(CH_2)_n$—Q—$(CH_2)_m$.

Representative $R^c$ groups are —$CH_3$, —COOH,

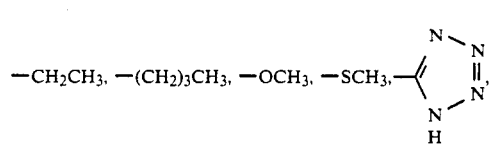

—$NHCH_2COOH$, —$CH_2OH$, —OH, —$CH_2COOH$,

—$CH_2CH_2COOH$, —$CH_2CONH_2$, —$CH_2CH_2S^+(CH_3)_2$,

—$CH_2CH_2SO_3H$, 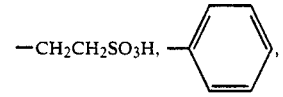

—$CONH_2$, —$SO_2NH_2$, —$SO_3H$, —$NH_2$, —$N(CH_3)_2$,

—$CON(CH_3)_2$, —$NHCH_3$, —$CH_2NH_2$, —CN, —$CH_2CN$,

—$CH_2SCH_3$, —$CH_2SO_3$, —$CH_2SOCH_3$, —$CH_2SO_2CH_3$,

—$SO_2CH_3$, —$SOCH_3$, —$CH_2OCH_3$, —$CH_2PO(OH)(OCH_3)$,

—$CF_3$, —$CH_2OC(O)NH_2$, —$CH_2SO_2NH_2$, —$SCH_2CH_2CN$, Br,

Cl, F, —$SCF_3$, —$CH_2SCF_3$, and —$SCH_2CF_3$.

The aliphatic cyclic hydrocarbon group has been conveniently represented throughout by the following formula:

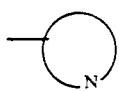

Useful examples of the aliphatic cyclic hydrocarbon group are set out below:

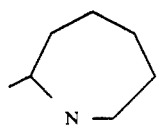 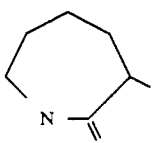 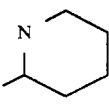

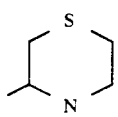 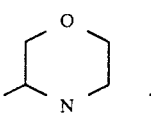 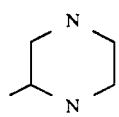

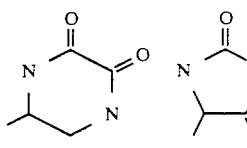 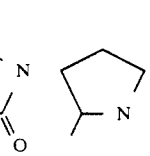

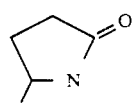 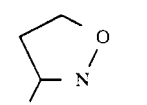 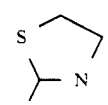

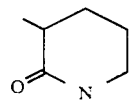 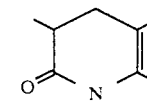 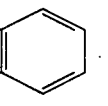

It is implied that attachment of the above group to the rest of the compound may be through any carbon atom of the ring, but is not through a heteroatom (i.e. N, S, or O). It is also implied that where the attachment creates a chiral center, the (R) and (S) configurations are understood.

With regard to all of the preferred substituents described above, the following compounds are preferred embodiments of the present invention:

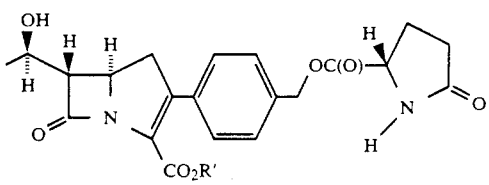

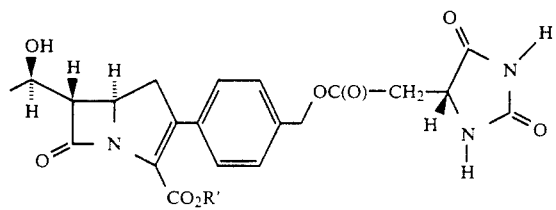

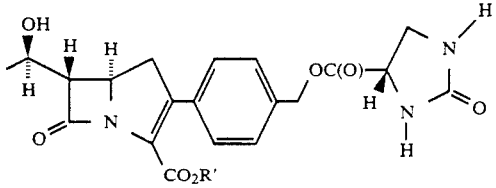

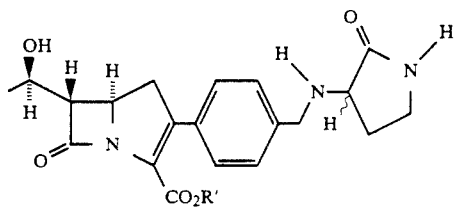

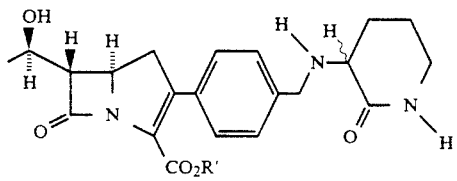

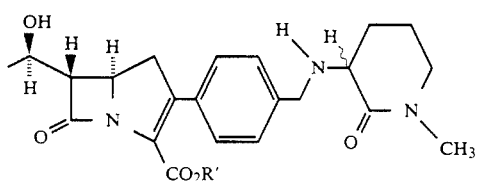

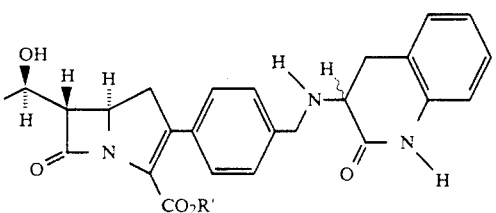

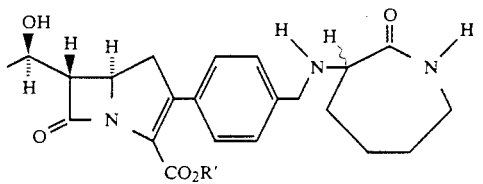

where M is a hydrogen, a negative charge ⁻, or a pharmaceutically acceptable salt or ester.

While R=H is usually preferred, there are instances in which R=$CH_3$ may provide improved chemical stability, water solubility, or pharmacokinetic behavior. The substituent R=$CH_3$ may be of either configuration, i.e., the α or β-stereoisomer.

For most of the compounds exemplified herein, the R substituent is hydrogen. This is the result not only of a more facile synthesis for such compounds, but also of a preference for R=hydrogen based on the superior antibacterial activity of such compounds.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non-toxic acid addition salts. In those cases where the Formula I compounds possess a basic functional group, they can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The compounds of the present invention are valuable antibacterial agents active against various Gram-positive and Gram-negative bacteria and accordingly find utility in human and veterinary medicine. Representative pathogens which are sensitive to the antibacterial agents of the present invention include various species or strains of the following: Staphylococcus, Enterococcus, Escherichia coli, Klebsiella, Enterobacter, Bacillus, Salmonella, Pseudomonas, Serratia, Proteus, and Bacterium. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. In general, a daily dosage consists of from about 5 to about 600 mg of active ingredient per kg of body weight of the subject in one or more treatments per day. A preferred daily dosage for adult human lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require use of a DHP inhibitor. However, such use is optional and contemplated to be a part of the present invention. Inhibitors of DHP and their use with carbapenem antibacterial agents are disclosed in the prior art [see European Patent Applications No. 79102616.4 filed Jul. 24, 1979 (Patent No. 0 010 573); 79102615.6, filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

DETAILED DESCRIPTION OF THE INVENTION

The carbapenem compounds of the present invention may be prepared in accordance with well known procedures in the art. Scheme 1 is particularly useful in illustrating the general procedure that is employed for the synthesis of a compound of the instant invention (when Q is NR$^g$). The substituents R, R$^1$, R$^2$, R$^a$, R$^b$ and R$^c$ are as defined hereinabove. It is understood that if any substituent R, R$^1$, R$^2$, R$^a$, R$^b$ or R$^c$ contains a functional moiety which is incompatible with a given reaction in the scheme, such a moiety may be protected or blocked by techniques known in the art. After the given reaction is performed the blocking/protecting group is removed by techniques known in the art.

Attachment of the spacer moiety "A" (in Scheme 1 "A" is —CH$_2$N(R$^g$)—) in Schemes 1 and 2 is at the position para to the carbapenem nucleus. This location is chosen only for convenience in drawing the formulae and it is understood that "A" may also be attached at the position meta to the carbapenem nucleus. The process of preparation of such analogs would be identical, but an appropriate phenyl Grignard would be employed in Step f in Scheme 1.

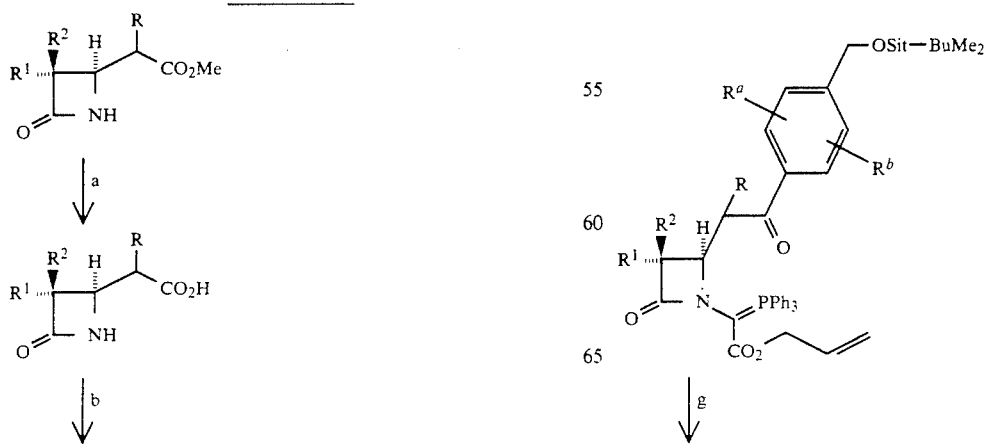

SCHEME 1

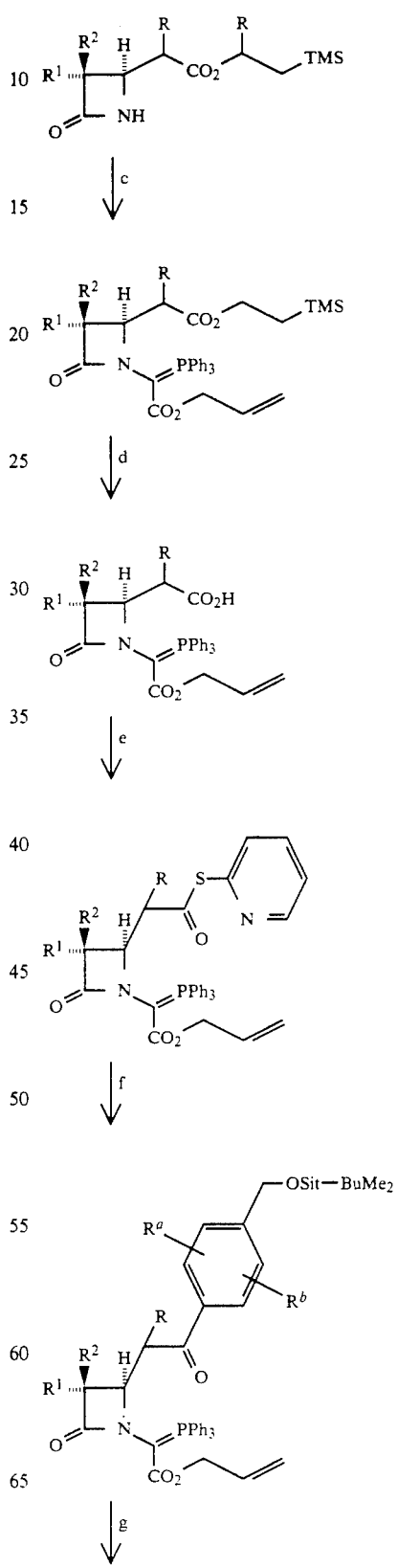

SCHEME 1 (continued)

[Structure I: β-lactam with R², R¹, R, and 4-(hydroxymethyl)phenyl substituent (Rᵃ, Rᵇ), N-CO₂-allyl, formed via Wittig from the phosphorane precursor with CO₂-allyl and PPh₃ groups]

↓ h

[Structure I: carbapenem with R², R¹, R, Rᵃ, Rᵇ, 4-CH₂OH-aryl, CO₂-allyl]

↓ i

[Structure II: carbapenem with CH₂J leaving group on aryl, CO₂-allyl]

↓ j

[Structure III: carbapenem with CH₂-N(Rᵍ)-(heterocycle with N-Rᵈ, R₍₁₋₃₎ᶜ), CO₂-allyl]

↓ k

[Structure IV: carbapenem with CH₂-N(Rᵍ)-(heterocycle with N⁺-Rᵈ), CO₂M]

a. NaOH/MeOH
b. carbonyl diimidazole
c. OHCCO₂-allyl, HO–CH₂CH₂–TMS;
   SOCl₂;
   Ph₃P
d. n-Bu₄NF
e. Pyr-ss-Pyr, Ph₃P f. BrMg–(aryl with Rᵃ, Rᵇ)–CH₂–OSi(Me)₂t-Bu
g. H₂SO₄/MeOH
h. xylenes, 145° C.
i. activate (J = —OMs, —OTf, —I)
j. RᵍHN–(ring with R₍₁₋₃₎ᶜ)–N–Rᵈ
k. (Ph₃P)₄Pd, Ph₃P
   C₇H₁₅CO₂H
   C₇H₁₅CO₂K The steps for preparing the 2-phenyl carbapenem intermediate I are well known in the art and are explained in ample detail in U.S. Pat. Nos. 4,260,627 and 4,543,257. Addition of the aliphatic heterocyclyl aminoalkyl moiety, generally represented by the formula:

$$R^d-N\underset{}{\bigcirc}-R_{(1-3)}^c \quad (-NR^g)$$

is as represented in the schematic diagram above.

However, it is also an embodiment of the present invention to include more —CH₂— moieties in "A", as defined further above. Preparation of such a homologous compounds is in accordance with the above schematic diagram.

In words relative to the equations, the hydroxyl group of carbapenem intermediate I may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate II (J=—OMs) may be converted to the more reactive iodide derivative by treatment with sodium iodide in a suitable solvent, e.g., acetone, at reduced or ambient temperatures. Alternatively, the hydroxyl group may be directly converted into the iodide group by common methods known in the art. For example, treatment of the hydroxyl group with methyl triphenoxyphosphonium iodide in a suitable solvent, such as dimethylformamide, at reduced or ambient temperatures, directly provides the desired iodide. Alternatively, the trifluoromethanesulfonate group may be generated in situ from an iodide group by treatment with excess silver trifluoromethanesulfonate in a suitable solvent, e.g., acetonitrile, at reduced temperatures.

The above are representative of suitable activating groups leaving groups: alkyl and substituted alkylsulfonates, aryl and substituted arylsulfonates, and halide. The common sulfonate activating groups are: methanesulfonyloxy, trifluoromethanesulfonyloxy, fluorosulfonyloxy, p-toluenesulfonyloxy, 2,4,6-triisopropylbenzene sulfonyloxy, p-bromobenzenesulfonyloxy and p-nitrobenzenesulfonyloxy. The preferred halo activating groups are bromo and iodo. These alkyl and arylsulfonate activating groups may be prepared using an analogous route to the one described above using the sulfonyl chloride or the sulfonic anhydride.

Once the desired activation has been carried out, introduction of the heterocyclylalkylamino group can then proceed. One of the following two procedures has been found suitable for such introduction.

Method A

When the activated group is iodide, the addition of the heterocyclylamino group, such as 3-(2-piperidonyl-)amino, is accomplished simply by treating the carbapenem intermediate II (J=iodo) with the corresponding heterocyclylamine, such as 3-amino-2-piperidone, in a suitable solvent, e.g., acetonitrile, at about room temperature.

Method B

When the activated group is trifluoromethanesulfonate, the carbapenem intermediate II (J=trifluoromethanesulfonate) is formed in situ by treatment of the carbapenem intermediate II (J=iodo) with excess silver trifluoromethanesulfonate in a suitable solvent, e.g., acetonitrile, at reduced temperatures. As with Method A, the heterocyclylamine is then added to the same reaction flask and displacement of the activated group then takes place directly.

In the preparation methods described above, the carboxyl group at the 3-position remains blocked by a carboxyl covering group until the final product is prepared. Thus, the product carbapenem intermediate III is deprotected by a palladium catalyzed de-esterification, as described by McCombie et al., J. Org. Chem., 47, 2505(1983). The carbapenem antibiotic IV is then obtained by conventional isolation/purification methodology known in the art.

Scheme 2 shows an alternative synthesis of the 2-phenyl-carbapenem I. This synthesis involves a palladium catalysed cross-coupling reaction between a carbapenem triflate and a suitably substituted arylstannane a process which is described in U.S. patent application Ser. No. 485,096 filed Feb. 26, 1990, hereby incorporated by reference. In order to apply this synthesis, it is first necessary to modify the substituted bromobenzene V to the trimethylstannylbenzene VI. This is accomplished by reacting V with t-butyllithium in THF at from −78° to −50° C. followed by the addition of trimethyltin chloride. This provides an intermediate from which the t-butyldimethylsilyl protecting group on the 9-position hydroxymethyl substituent is removed by exposure to tetra-n-butylammonium fluoride in THF yielding VI. If the t-butyldimethylsilyl group was removed from carbapenem IX under the same conditions, a substantial portion of the carbapenem would be degraded and lost. Thus modification of the precursor substituent in this instance and replacement with another precursor substituent or even $R^a$ is best performed before attachment to the carbapenem. Referring to Scheme 2, the 2-oxocarbapenem VII is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran. An organic nitrogen base, such as triethylamine and the like, is then added to the reaction solution followed immediately by a silylating agent, such as trimethylsilyl trifluoromethanesulfonate to provide intermediate VIII. An aprotic polar coordinating solvent, such as DMF, 1-methyl-2-pyrrolidinone and the like, is added. This is followed by the addition of a palladium compound, such as tris(dibenzylideneacetone)dipalladiumchloroform, palladium acetate and the like, a suitably substituted phenylphosphine, such as tris(4-methoxyphenyl)phosphine, tris(2,4,6-trimethoxyphenyl)phosphine and the like, and the stannane VI. A metal halide, such as lithium chloride, zinc chloride and the like, is added and the reaction solution is quickly warmed to a suitable temperature, such as 0° to 50° C., and allowed to stir for a suitable amount of time. The carbapenem IX is obtained by conventional isolation/purification methodology known in the art. Final elaboration of bridge-nitrogen containing heterocyclic group from a precursor substituent, e.g. hydroxymethyl, may be accomplished on carbapenem intermediate IX. Removal of protecting groups then provides the final compound of Formula IV. Such final elaboration and deprotection is described in further detail below.

SCHEME 2

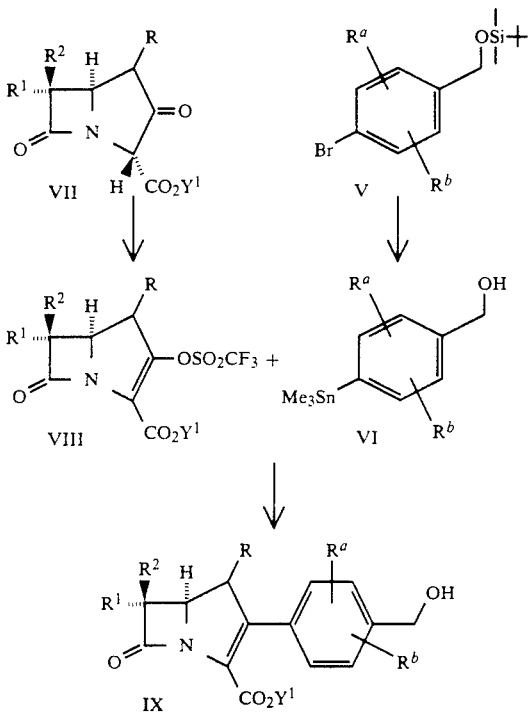

The bridging element "A" which contains a carbonyloxy moiety, is also an embodiment of the present invention. Preparation of compounds containing such a carbonyloxy bridge is in accordance with the following synthetic scheme, Scheme 3.

SCHEME 3

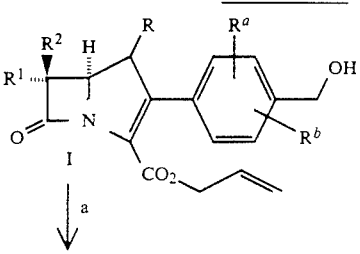

-continued
SCHEME 3

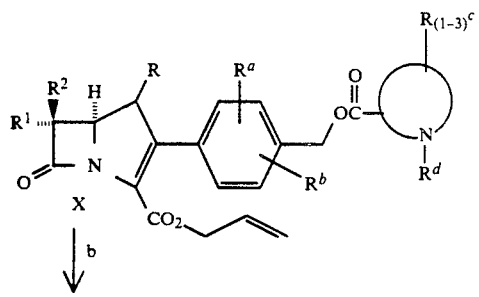

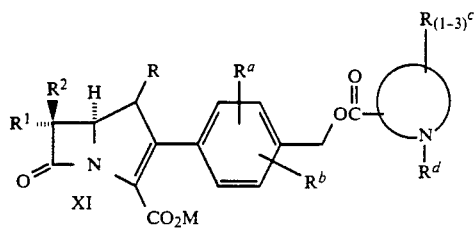

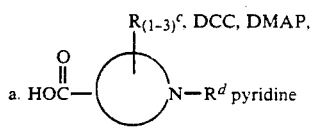

a. HOC—◯—N—R$^d$ pyridine  R$_{(1-3)}^c$, DCC, DMAP, b. (Ph$_3$P)$_4$Pd, Ph$_3$P
C$_7$H$_{15}$CO$_2$H, C$_7$H$_{15}$CO$_2$K In words relative to the equations a mixture of a heterocyclylcarboxylic acid, such as 2-pyrrolidone-5-carboxylic acid and the like, and the carbapenem intermediate I was treated with an acid activating agent, such as dicyclohexylcarbodiimide (DCC), in a suitable solvent, such as pyridine. The reaction may benefit from the presence of a hindered organic nitrogen base, such as 4-(N,N-dimethylamino)pyridine. The product, carbapenem intermediate V, is obtained by conventional isolation/purification methodology known in the art. Palladium (O) catalyzed de-esterification of intermediate X as described hereinabove provides the carbapenem antibiotic XI Where the heterocyclyl group has one or more substituents R$^c$, the most facile method of providing such a substituent is to employ as the reactant in the preparation methods described above a heterocyclyl compound which already has the desired substituent(s). Such substituted heterocyclyl compounds are readily available starting materials or may be prepared in a straight-forward manner using known literature methods.

Scheme 4 is particularly useful in illustrating the more specific procedure that is employed for the synthesis of a compound of the instant invention wherein R$^1$ is (R)—CH3CH(OH)—, R$^2$ is hydrogen and R$^a$ and R$^b$ are both hydrogen. These definitions of R$^1$ and R$^2$ are the most preferred embodiment of the instant invention. The substituents R and R$^c$ are as defined herein above. It is understood that if any substituent R$^c$ contains a functional moiety which is incompatible with a given reaction in the scheme, such a moiety may be protected or blocked by techniques known in the art. After the given reaction is performed the blocking/protecting group is removed by techniques known in the art.

SCHEME 4

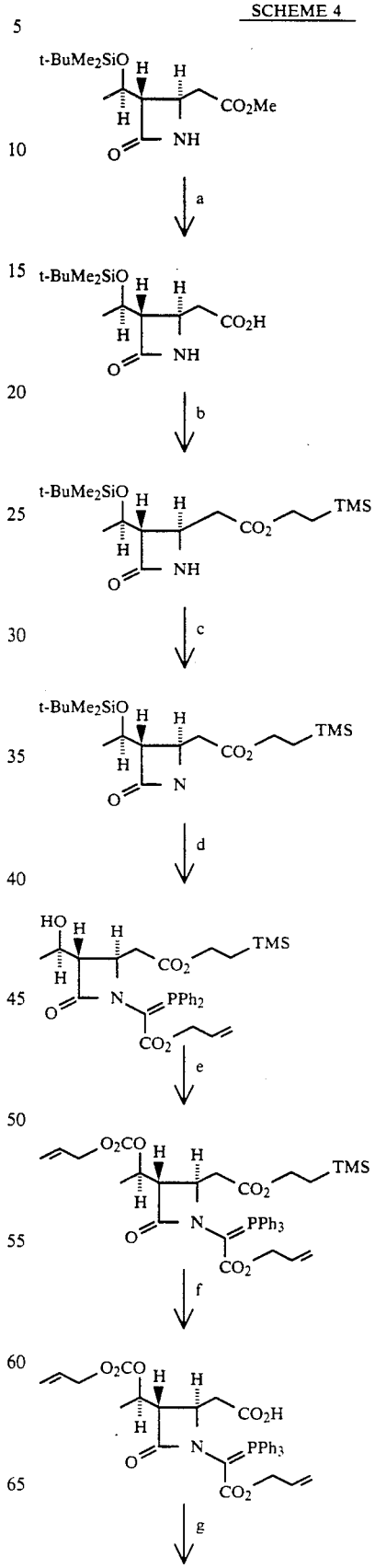

19

-continued
SCHEME 4

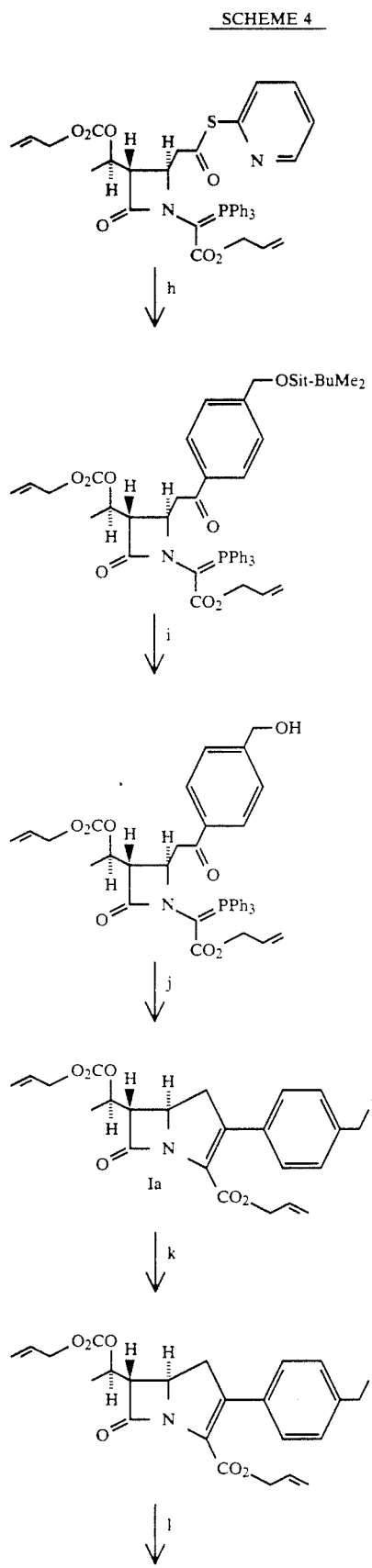

20

-continued
SCHEME 4

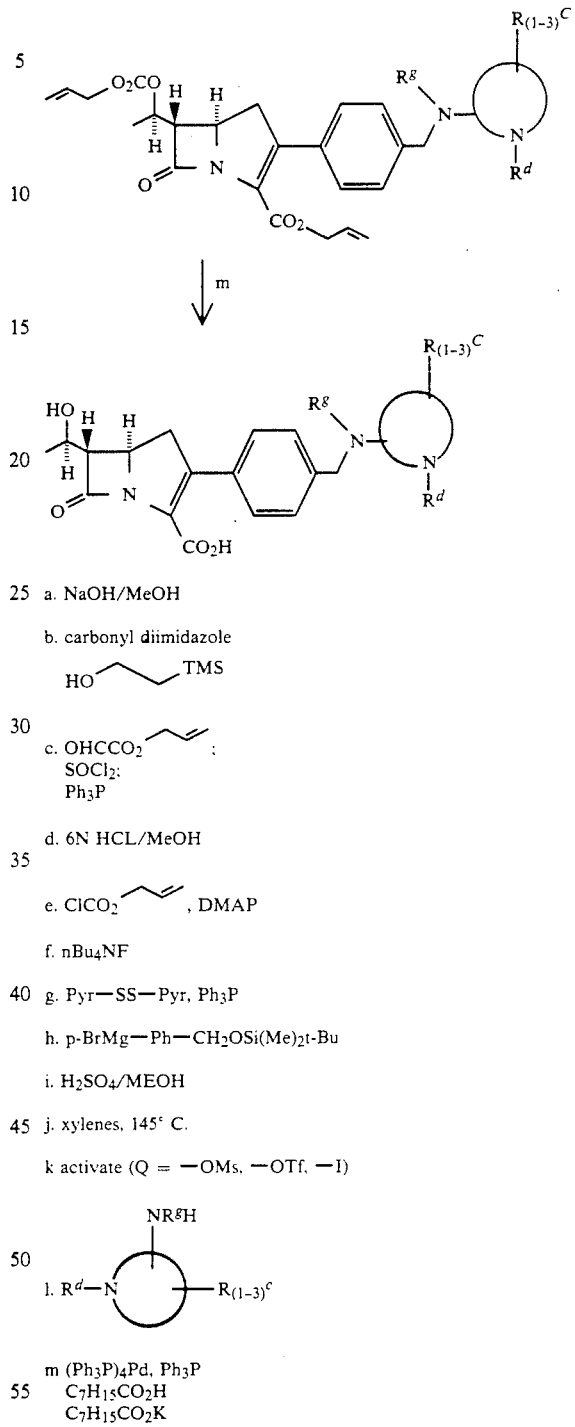

a. NaOH/MeOH b. carbonyl diimidazole
   HO—CH₂CH₂—TMS c. OHCCO₂—allyl ;
   SOCl₂;
   Ph₃P d. 6N HCL/MeOH e. ClCO₂—allyl, DMAP f. nBu₄NF g. Pyr—SS—Pyr, Ph₃P h. p-BrMg—Ph—CH₂OSi(Me)₂t-Bu i. H₂SO₄/MEOH j. xylenes, 145° C.

k activate (Q = —OMs, —OTf, —I)

l. $R^d$—N(ring)—$R_{(1-3)}^c$ with NR$^g$H m (Ph₃P)₄Pd, Ph₃P
  C₇H₁₅CO₂H
  C₇H₁₅CO₂K The steps for preparing the 2-phenyl carbapenem intermediate Ia are well known in the art and are explained in ample detail in U.S. Pat. Nos. 4,260,627 and 4,543,257.

The synthesis illustrated in Scheme 4 and the particular exemplifications which follow show the 6-(1-hydroxyethyl) moiety, which is preferred in most cases. However, it has been found that with certain 2-sidechain selections, the ultimate balance of favorable clinical properties in the overall molecule may be enhanced by selection of the 6-(1R-fluoroethyl) moiety instead.

Preparation of this and other 6-fluoroalkyl compounds within the scope of the present invention may be carried out in a straightforward manner using techniques well known in the art of preparing carbapenem antibacterial compounds. See, e.g., J. G. deVries et al., *Heterocycles*, 23 (8), 1915 (1985); J6-0163-882-A (Sanraku Ocean).

For all the compounds exemplified hereinbelow, the R substituent is hydrogen, which is preferred. However, when R=methyl, the analogous 6-(1-hydroxyethyl) and 6-(1-fluoroethyl)carbapenems of the present invention are prepared in the manner described herein utilizing the appropriately chosen synthons which are known in the art. See, for example, L. M. Fuentes, I. Shinkai, and T. N. Salzmann, *JACS*, 108, 4675 (1986); and BE-900-718-A (Sandoz) respectively.

Similarly, if R1 is (R)—CH3CH(OH)—, R2 is hydrogen, both Ra and Rb are hydrogen and the bridging element contains a carbonyloxy moiety, the following Scheme 5 is illustrative of the preparation of such compounds.

EXAMPLE 1

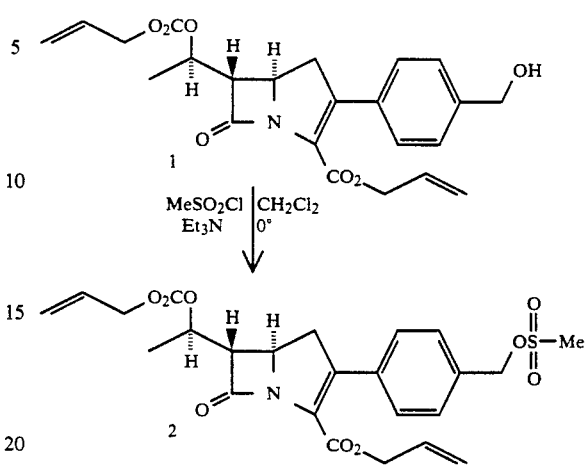

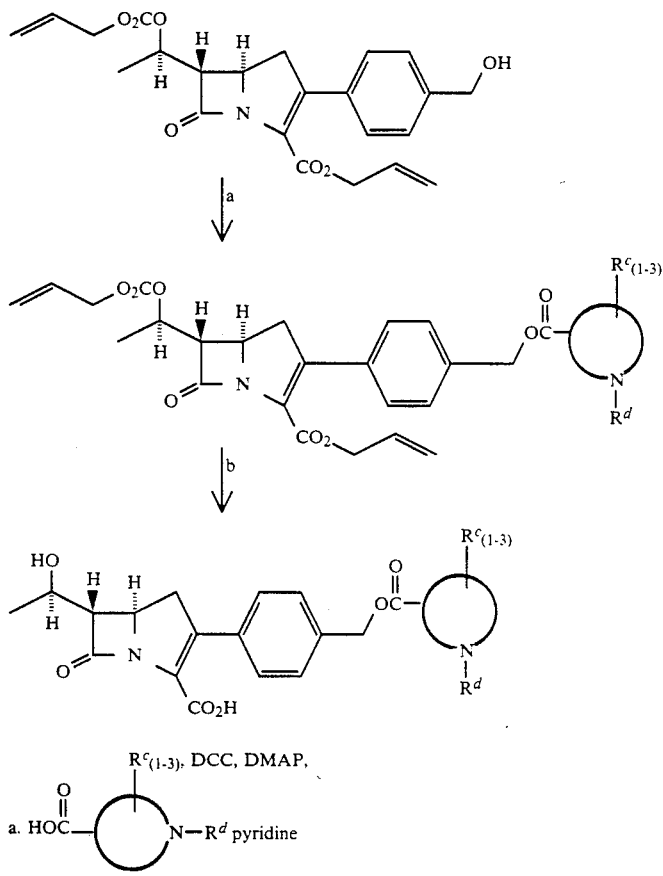

b. $(Ph_3P)_4Pd$, $Ph_3P$
$C_7H_{15}CO_2H$; $C_7H_{15}CO_2K$

The invention is further defined by reference to the following examples, which are intended to be illustrative and not limiting. All temperatures are in degrees Celsius.

Allyl-(5R,6S)-2-(4-methanesulfonyloxymethylphenyl)-6-[1R-(allyloxycarbonyloxy)ethyl]carbapen-2-em-3-carboxylate (2)

To a stirred solution of 42.7 mg (0.1 mmole) of 1 in 1 ml of sieve dried $CH_2Cl_2$ at 0° C. under a nitrogen atmosphere was added sequentially 15.2 mg (0.15 mmole) of neat Et₃N and then 14.9 mg (0.13 mmole) of neat mesyl chloride. The resulting mixture was stirred for 15 minutes, and then partitioned between EtOAc, ice-H₂O, and some 2N HCl. The organic phase was separated, washed with saturated NaCl solution, dried over Na₂SO₄, filtered, evaporated, and dried in vacuo to give a quantitative yield of 2; IR (CH₂Cl₂): 1780, 1745, 1725 cm⁻¹; 200 MHz ¹H-NMR (CDCl₃): δ 1.49 (d, J=6.4 Hz, C$\underline{H_3}$CH), 2.96 (s, C$\underline{H}$SO₃), 3.18 (dd, J=9.9, 18.1 Hz, H-1), 3.34 (dd, J=8.9, 18.1 Hz, H-1), 3.43 (dd, J=2.8, 8.1 Hz, H-6), 4.30 (dt. J=2.3, 2.8, 9.9 Hz, H-5), 4.66 (m, CH₃C$\underline{H}$OH and C$\underline{H_2}$CH=CH₂), 5.26 (m, OCH₂C$\underline{H}$=C$\underline{H_2}$), 5.29 (s, ArC$\underline{H_2}$OSO₂), 7.40 (s, Ar—H). UV: $\lambda_{max}^{p\text{-}diox}$=314 nm.

EXAMPLE 2

(0.15 mmole) of NaI. The ice-H₂O bath was removed and the mixture stirred further under a nitrogen atmosphere for 0.5 hour. After this time, the resulting mixture was partitioned between EtOAc, ice-H₂O, 5% Na₂S₂O₄ (aq.) solution and saturated NaCl solution. The organic phase was separated, dried over Na₂SO₄, filtered, evaporated and dried in vacuo to give 3; IR (CH₂Cl₂): 1780, 1745, 1725 cm⁻¹; 200 MHz ¹H-NMR (CDCl₃): δ 1.49 (d, J=7.4 Hz, CH₃), 3.17 (dd, J=9.8, 18.1 Hz, H-1), 3.29 (dd, J=8.7, 18.1 Hz, H-1), 3.41 (dd, J=2.9, 8.7 Hz, H-6), 4.27 (dt, J=2.9, 8.7, 9.8 Hz, H-5), 4.65 (m, CH₃C$\underline{H}$OH and OC$\underline{H_2}$CH=CH₂), 5.26 (m, OCH₂C$\underline{H}$=C$\underline{H_2}$), 5.89 (m, OC$\underline{H_2}$C$\underline{H}$=CH₂), 7.32 (m, Ar-H). UV: $\lambda_{max}^{p\text{-}diox}$=322 nm.

EXAMPLE 3

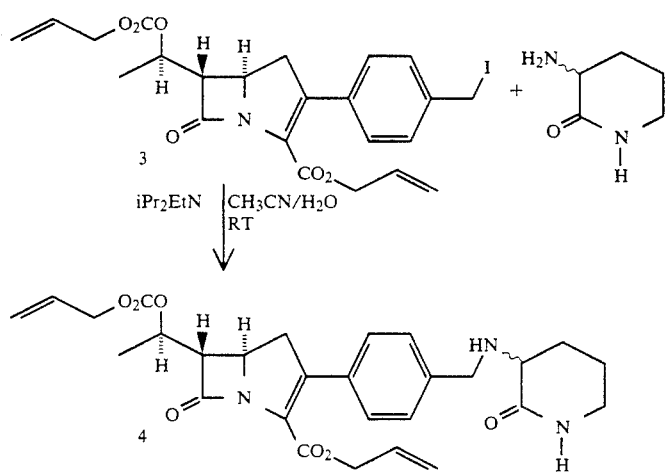

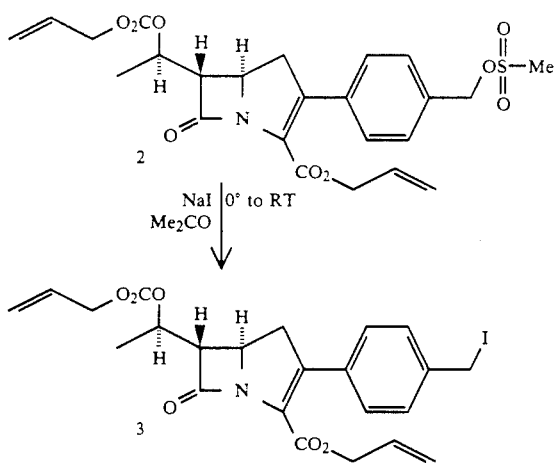

Allyl-(5R,6S)-2-(4-iodomethylphenyl)-6-[1R-(allyloxycarbonyloxy)ethyl]-carbapen-2-em-3-carboxylate (3)

To a stirred solution of 38.8 mg (0.077 mmole) of 2 in 1 ml of acetone at 0° C. was added all at once 23 mg Allyl-(5R,6S)-2-(4-[3-(2-piperidonyl)aminomethyl]-phenyl)-6-[1R-(allyloxycarbonyloxy)ethyl]carbapen-2-em-3-carboxylate (4)

A suspension of 154 mg of 3-amino-2-piperidone hydrochloride in 5 mL of acetonitrile was treated with 0.186 mL of diisopropylethylamine and 0.175 mL of water was added to dissolve any remaining insoluble materials. A solution of 262 mg of compound 3 in 2 mL of acetonitrile was added and the reaction mixture was stirred overnight at room temperature (RT). The reaction mixture was then concentrated under vacuum and the residue was then partitioned between EtOAc and water. The separated organic solution was washed with brine and dried with anhydrous sodium sulfate. The mixture was filtered and the filtrate concentrated under vacuum. Chromatography of the residue over silica gel (9:1 EtOAc:hex.) provided 57 mg of compound 4.

200 MHz ¹H-NMR (CDCl₃): δ 1.5 (d. 3H), 1.9 (m, 7H), 3.3 (m, 6H), 3.9 (q, 2H), 4.3 (dt, 1H), 4.7 (m, 4H), 5.2 (m, 4H), 5.8 (m, 2H), 7.4 ppm (s, 4H).

EXAMPLE 4

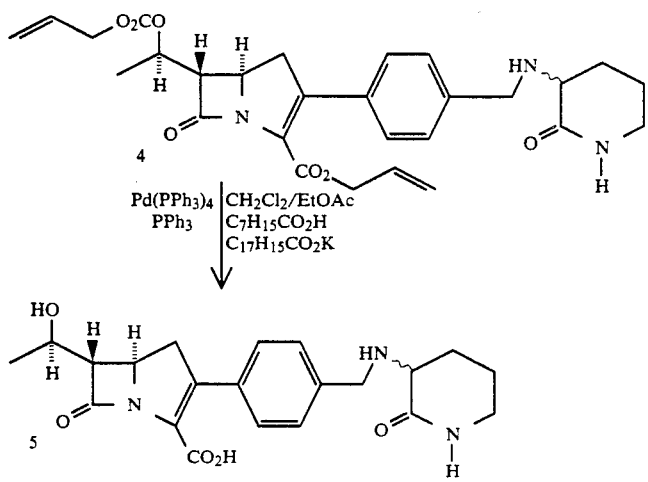

(5R,6S)-2-(4-[3-(2-Piperidonyl)aminomethyl]-phenyl)-6-[1R-hydroxyethyl]carbapen-2-em-3-carboxylic acid (5)

In 3 ml of dichloromethane and 2 ml of ethyl acetate there was dissolved the crude product of Example 3, 2-[4-(3-[piperidin-2-onyl]aminomethyl-4-phenyl)carbapenem (4.) (25 mg, 0.048 mmole), and the solution was cooled under nitrogen atmosphere to 0° C. 0.5M Potassium 2-ethylhexanoate in ethyl acetate solution (0.105 μl, 0.053 mmole) was added followed by 2-ethylhexanoic acid (7.6 μl, 0.048 mmole), triphenylphosphine (3.8 mg, 0.014 mmole) and tetrakis triphenylphosphinepalladium (5.5 mg, 0.005 mmole). The reaction mixture was then stirred for 3.0 hours at room temperature, after which time the reaction slurry was diluted with methylene chloride and the mixture was then extracted 2× with water. The combined extracts were concentrated under vacuum to a small volume and the concentrated solution was chromatographed over reverse phase silica gel (7% THF in water) to provide compound 5

200 MHz $^1$H NMR (D$_2$O): δ 1.4 (d, 3H), 2.2 (broad m, 4H), 3.2 (m, 1H), 3.5 (m, 4H), 3.9 (m, 1H) 4.3 (m, 4H), 7.5 ppm (s, 4H);

UV $\lambda_{max}^{H2O}$ = 303 nm.

EXAMPLE 5-9

Employing the procedures described above, additional compounds of the present invention were prepared. These are described in the table below, which additionally includes characterizing data.

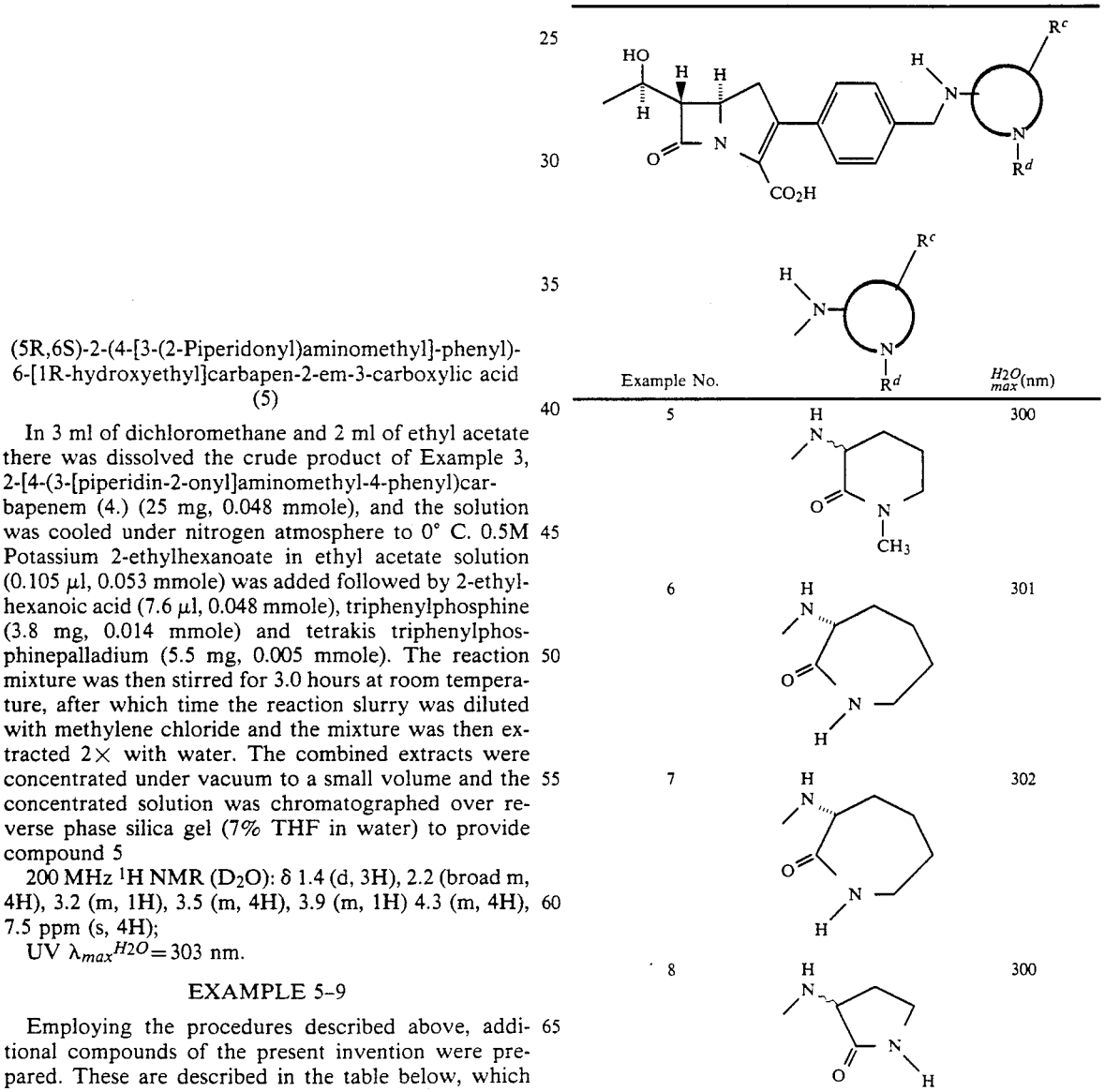

27
-continued

28
EXAMPLE 10

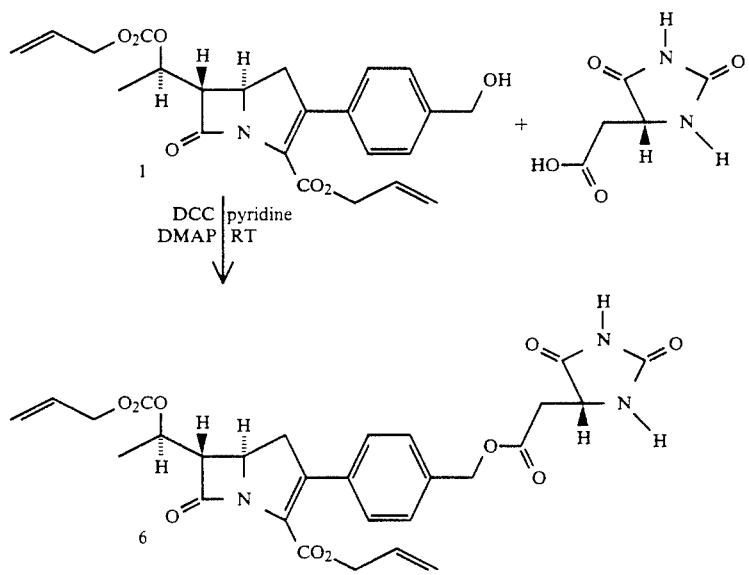

Allyl-(5R,6S)-2-(4-[5-(2,4-imidazolidinedionyl)-carbonyloxymethyl]phenyl)-6-[1R-(allyloxy-carbonyloxy)ethyl]carbapen-2-em-3-carboxylate (6)

5-Hydantoinacetic acid (69 mg) was dissolved (with heat) in 1 mL of pyridine and the solution (after cooling to RT) was added to a flask containing 133 mg of compound 1. The solution was diluted with 0.7 mL of pyridine and 92 mg of dicyclohexylcarbodiimide and 13 mg of 4-(N,N-dimethylamino)pyridine was added. The reaction mixture was stirred for 2 hours at RT, then filtered and the filtrate concentrated under vacuum. The residue was dissolved in diethyl ether and filtered and the filtrate washed 2x with aqueous 5% sodium sulfate solution. The organic phase was dried with magnesium sulfate, filtered and concentrated under vacuum. Chromatography of the residue over silica gel (4:1 EtOAc:hexane) provided 43 mg of compound 6. 200 MHz $^1$H-NMR (CDCl$_3$): δ 1.5 (d, CH$_3$), 2.7 (q, 1H), 3.1 (dd, 1H), 3.3 (t, 2H), 3.45 (dd, 1H), 4.3 (m, 3H), 4.7 (m, 3H), 5.25 (m, 6H), 5.9 (m, 2H), 6.3 (d, 2H), 7.3 (q, 4), 8.5 ppm (s,1H).

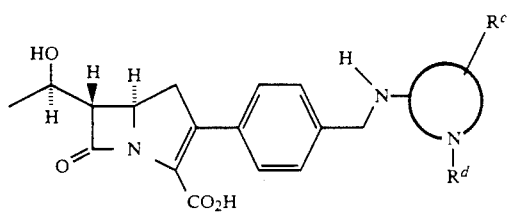

| Example No. | $R^c$, $R^d$ | $H2O \atop max$(nm) |
|---|---|---|
| 9 | 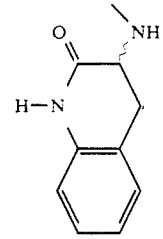 | 250, 300 |

EXAMPLE 11

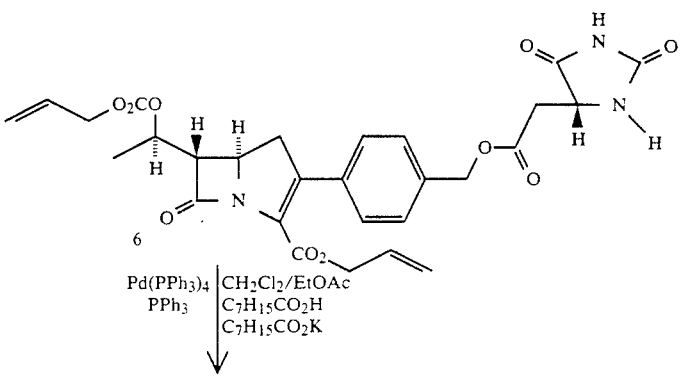

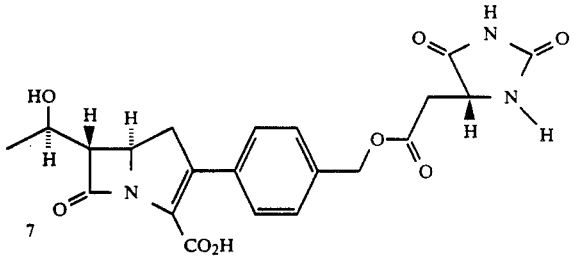

(5R,6S)-2-(4-[5-(2,4-Imidazolidinedionyl)carbonyloxymethyl]phenyl)-6-[1R-hydroxyethyl]carbapen-2-em-3-carboxylate (7)

In 1.5 ml of dichloromethane and 1.5 ml of ethyl acetate there was dissolved the product 6 of Example 10 (43 mg, 0.0758 mmole), and the solution was cooled under nitrogen atmosphere to 0° C. 2-Ethylhexanoic acid (0.27 μl, 0.17 mmole) and 0.5M potassium 2-ethylhexanoate in ethyl acetate solution (0.400 μl, 0.20 mmole) were then added, followed by a solid mixture of triphenylphosphine (13 mg, 0.05 mmole) and tetrakis triphenylphosphinepalladium (23 mg, 0.02 mmole) The reaction mixture was then stirred for 3.0 hours at room temperature, after which time the mixture was diluted with 1 mL methylene chloride extracted 2× with water. The combined extracts were concentrated under vacuum to a small volume and the concentrated solution was chromatographed over reverse phase silica gel (5% THF in water) to provide 15.3 mg of compound 7.

200 MHz $^1$H NMR (D$_2$O): δ 1.45 (d, 3H), 3.2 (m, 3H), 3.6 (m, 2H), 4.4 (m, 2H), 4.7 (t, 1H), 5.3 (q, 2H), 7.5 ppm (s, 4H);

UV $\lambda_{max}^{H2O}$ = 301 nm.

EXAMPLES 12-13

Employing the procedures described above, in Examples 10 and 11, additional compounds of the present invention were prepared. These are described in the table below, which additionally includes characterizing data.

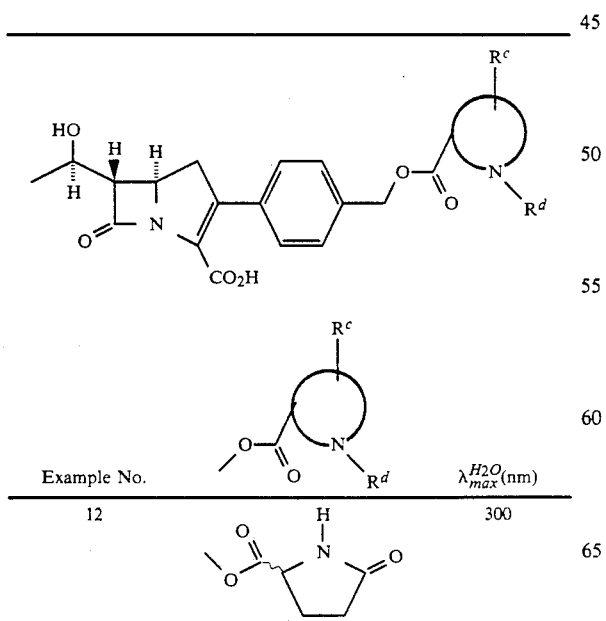

| Example No. | | $\lambda_{max}^{H2O}$(nm) |
|---|---|---|
| 12 | | 300 |
| 13 | | 303 |

What is claimed is:

1. A compound of the formula:

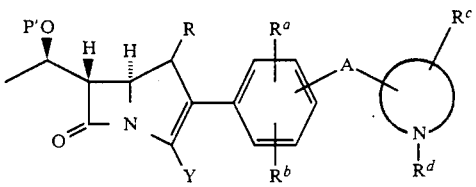

wherein:

R is H or CH$_3$;

P' is: a readily removable protecting group for hydroxy;

R$^a$ and R$^b$, are independently selected from the group consisting of hydrogen and the radicals set out below:

a) a trifluoromethyl group: —CF$_3$;
b) a halogen atom: —Br, —Cl, —F, or —I;
c) C$_1$-C$_4$ alkoxy radical: —OC$_{1-4}$ alkyl, wherein the alkyl is optionally mono-substituted by R$^q$, where R$^q$ is a member selected from the group consisting of —OH, —OP', —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl, phenyl or M defined below), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal or M defined below);

d) a hydroxy or protected hydroxy: —OH or —OP';

e) a carbonyloxy radical: —O(C=O)R$^s$, where R$^s$ is C$_{1-4}$ alkyl or phenyl, each of which is optionally mono-substituted by R$^q$ as defined above;

f) a carbamoyloxy radical: —O(C=O)N(R$^y$)R$^z$ where R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)—, —S(O)$_2$— or —NR$^e$—, to form a ring (where R$^e$ is hydrogen, C$_1$-C$_4$alkyl, and C$_1$-C$_4$alkyl mono-substituted with R$^q$ and the ring is optionally mono-substituted with R$^q$ as defined above);

g) a sulfur radical: —S(O)$_n$—R$^S$ where n=0-2, and R$^S$ is defined above;

h) a sulfamoyl group: —SO$_2$N(R$^y$)R$^z$ where R$^y$ and R$^z$ are as defined above;

i) azido: N$_3$ j) a formamido group: —N(R$^t$)(C=O)H, where R$^t$ is H or C$_{1-4}$ alkyl, and the alkyl thereof is optionally mono-substituted by R$^q$ as defined above;

k) a (C$_1$-C$_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;

l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;

m) a ureido group: —N(R$^t$) (C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as define above;

r) carbonyl radical: —(C=O)R$^s$, where R$^s$ is as defined above;

s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;

t) a (C$_1$-C$_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N(C$_1$-C$_4$ alkoxy)carbamoyl radical in which the nitrogen atom may be additionally substituted by a C$_1$-C$_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono (P=O(OM$^b$)$_2$); alkylphosphono {P=O(OM$^b$)—(O(C$_1$-C$_4$ alkyl))}; alkylphosphinyl (P=O(OM$^b$)—(C$_1$-C$_4$alkyl)); phosphoramido (P=O(OM$^b$)N(R$^y$)R$^z$) and P=O(OM$^b$)NHR$^x$); sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl; M$^b$ is as defined above; and R$^y$ and R$^z$ are as defined above;

ac) C$_2$-C$_4$ alkenyl radical, optionally mono-substituted by one of the substituents a) to ab) above and phenyl which is optionally substituted by R$^q$ as defined above;

ad) C$_2$-C$_4$ alkynyl radical, optionally mono-substituted by one of the substituents a) to ab) above;

ae) C$_1$-C$_4$ alkyl radical;

af) C$_1$-C$_4$ alkyl mono-substituted by one of the substituents a)-ab) above;

ag) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to af) above;

R$^c$ is hydrogen, C$_1$-C$_6$ alkyl or R$^q$ defined hereinabove;

R$^d$ is hydrogen, NH$_2$, O or C$_1$-C$_4$alkyl (where the alkyl group is optionally mono-substituted with R$^q$ as defined above);

A is para (p) or meta (m) with respect to the point of attachment of the phenyl ring to the carbapenem nucleus, and is (CH$_2$)$_m$—Q—(CH$_2$)$_n$, where m is 1 to 2 and n is 0 to 2; and Q is O(C=O) or NR$^g$; where R$^g$ is hydrogen or C$_1$-C$_6$ alkyl;

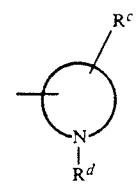

is selected from the group consisting of:

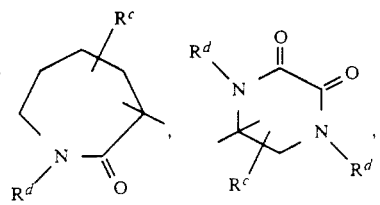

-continued

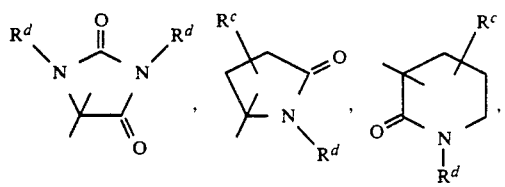

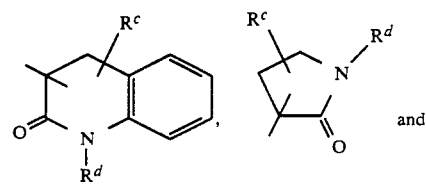 and

-continued

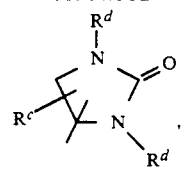, wherein $R^c$ and $R^d$ are as defined above;

Y is —COOY' where Y' is readily removable protecting group for carboxy and —COOY' is not a pharmaceutically acceptable ester; and $R^a$, $R^b$, $R^c$ and $R^d$ are defined above.

2. The compound of claim 1 wherein $R^c$ is hydrogen and $R^d$ is hydrogen.

3. The compound of claim 1 wherein P' is selected from the group consisting of methoxy-t-butylphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

* * * * *